(12) United States Patent
Bharathi et al.

(10) Patent No.: US 7,063,974 B2
(45) Date of Patent: Jun. 20, 2006

(54) BARODURIC BACTERIUM FROM INDIAN OCEAN

(75) Inventors: Ponnapakkam Adikesavan Loka Bharathi, Goa (IN); Shanta Nair, Goa (IN); Dorairajasingham Chandramohan, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 43 days.

(21) Appl. No.: 10/645,131

(22) Filed: Aug. 21, 2003

(65) Prior Publication Data

US 2004/0043090 A1    Mar. 4, 2004

Related U.S. Application Data

(62) Division of application No. 09/825,406, filed on Apr. 3, 2001, now Pat. No. 6,669,944.

(51) Int. Cl.
*C12N 1/12* (2006.01)
(52) U.S. Cl. .............. 435/252.1; 435/243; 435/252.32; 424/93.4; 424/234.1; 424/780
(58) Field of Classification Search ............. 435/243, 435/252.1, 252.32; 424/93.4, 780, 234.1
See application file for complete search history.

(56) References Cited

U.S. PATENT DOCUMENTS 5,885,767 A * 3/1999 Rozzell, Jr. .................... 435/4

OTHER PUBLICATIONS

Funke et al., "Antimicrobial Susceptibility Patterns of Some Recently Established Coryneform Bacteria", Antimicrobial Agents and Chemotherapy, Dec. 1996, vol. 40, No. 12, pp. 2874-2878.*

* cited by examiner

*Primary Examiner*—Leon B. Lankford
(74) *Attorney, Agent, or Firm*—John P. White, Esq.; Cooper & Dunham LLP (57) ABSTRACT

Accordingly the present invention provides a process for the preparation an alcoholic extract with Carotenoids, UV absorption, antibacterial and pH indicating properties from a deep-sea bacterium which comprises a method for growing the cells in a medium with salinity ranging from 1.5 to 3% for 3–4 days at 28+/−2° C. and harvesting them to prepare an extract which shows the properties of carotenoids (yellow/orange coloration), UV absorption, antibacterial and pH indicator properties.

5 Claims, 5 Drawing Sheets

Application: Scanning
Data Name: DEFAULT
Start Wavelength: 260.0
Stop Wavelength: 550.0
Time:           0.0
Temperature:    -------

PEAK TABLE
WL: 448.0 nm    DATA:   0.564

BARODURIC BACTERIUM FROM INDIAN OCEAN

This application is a divisional of U.S. Ser. No. 09/825,406, filed Apr. 3, 2001, now U.S. Pat. No. 6,669,944, the entire contents of which is hereby incorporated by reference into this application.

FIELD OF THE INVENTION

The present investigation relates to a process for the preparation of an extract with Carotenoids, UV absorption, antibacterial and pH indicating from a deep-sea bacterium for applications in food and cosmetic industries. The extract could be used as food and feed additives (colorant), food and feed preservatives and radio protective/sunscreen compound in cosmetics.

BACKGROUND AND PRIOR ART REFERENCES

A number of bacteria are known to produce several secondary metabolites like pigments, toxins, growth promoting compounds and antibiotics (Bushell Mo., 1982, Microbial aspects of the discovery of novel secondary metabolites, Top. Enzyme-Ferment Biotech no 1 6, 32–67). These bacteria have an added advantage in that they are easily replenishable as their generation time is much shorter than other microbes and higher organisms. Besides, their products are eco-friendly and can be used either in their native form or with minor modifications.

The synthetic pigments and dyes have proved to be more harmful than natural products. Some of the synthetic colours are either banned or the permissible concentrations drastically reduced. In the Government of India notification an amendment to the Prevention of Food Adulteration Act in March 1993 banned the use of permitted colours (The Navhind Times dated Aug. 4, 1998) European Union is planning to ban about 300 textile dyes containing chemicals known to increase the risk of cancer. Dyes containing significant levels of 22 of the so-called aromatic amines are known to be carcinogenic (The Navhind Times, dated Oct. 4, 1999). The planned legislation would phase out dyes that are used in textile, leather goods, seat covers, gloves. In short any material having even temporary contact with the skin, public's inclination towards bio pigments and colours is strong.

Pigments are known to be the most important secondary metabolites of organisms for various applications. Even though pigments can be produced by chemical synthesis there has been increasing demand and renewed interest for natural pigments. This is essentially due to the public awareness of the superiority and safety of natural products over the synthetic ones, especially in the food industry.

Reference may be made to the natural colorants like red betalin pigment from plant, *Beta vulgaris*. (Smith MAL, Dustin I, Leathers R, Zryd Jp 1992. Development of automated vision techniques for immediate analysis and control of betalin producing cultures. Hortiscience 27 (6), 572) or bright colour from the bryozoan animal, *Bugula dentata* (Matsunaga S, Fusetani N, Hashimoto K, 1986. Bioactive marine metabolites. VIII Isolation of an antimicrobial blue pigment from the bryozoan *Bugula dentata* Experientia 42(1), 84). However, use of such pigments from higher organisms has got certain limitation. For example the major drawbacks are that higher plants and animals have a longer generation time and the resources are limited. Though tissue culture has evolved as an alternate method to produce the cells for pigment extraction, the techniques are not always simple and have limited application. On the other hand, microbes, especially bacteria, can be exploited more advantageously for reasons mentioned above.

Among the pigments yellow-orange to red pigments, mostly belonging to the carotenoid group has been popular for various applications. For example, B carotene is a valuable metabolite and is in great demand in the food industry and Aquaculture (Michel P J, Dujardin E, Sironval C1995. Growth of *Dunalliella bardawil* under carotogenic conditions. J. Mar. Biotech no1 2 (2), 101–104). Carotenoids possessing carbonyl groups inhibit lipid peroxidation better than those lacking carbonyl groups (Michel P J, Dujardin E, Sironval C, 1995. Growth of *Dunalliella bardawil* under carotogenic conditions. J. Mar. Biotechnol 2 (2), 101–104). Despite the enormous economic potential of carotenoids, only a few of the microbes have been exploited commercially. Zeaxanthin, a carotenoid, from a bacterium (*Alteromonas* sp) is used in the food industry essentially for imparting colour to the product (Japanese patent No. JP-5049497). The same compound from another bacterium *Flavobacterium* sp (Nelis H J, De Leenheer A P 1991. Microbial sources of carotenoids pigments used in foods and feeds. J of Appl Bacterial 70, 181–191. U.S. Pat. Nos. 841,967, 3,951,742, 3,951,743, 4,026,949) has also been reported. A formulation of zeaxanthin from *Flavobacterium multivorans* is also claimed to prevent degeneration of macula in the iris of the eye (U.S. Pat. No. 5827652). Astaxanthin, another carotenoid from the yeast, *Phaffia rhodozyme* (Nelis H J, De Leenheer A P 1991. Microbial sources of carotenoid pigments used in foods and feeds. J of Appl Bacteriol 70, 181–191) has been reported to be useful as growth promoters Another group of pigments like menaquinones extracted from bacteria have also been used for various applications. A process has been claimed for the preparation of menaquinone-containing substance from *Bacillus subtilis* in food and drink preparations for osteoporosis therapy (JP-11032787). Pigments from *Brevibacterium* species have been used in the dairy products especially for ripening and flavouring cheese (Reyser E T, Maisnier-Patin S, Gratadoux J J & Richard J 1994. Isolation and identification of cheese smear bacteria inhibitory to *Listeria* spp. Int. J Food Microbiol. 21, 237–246) and production of menatetrone (JP-63267283; JP-61173792; EP-202613).

Japanese Patent No. 95-05169, titled: "Cosmetic containing fermented *Streptomyces* sp." describes "a new cosmetic preparation contains fermentation broth from *Streptomyces* sp. G172 (FERM P-13630), grown in culture medium at 25–30 deg for 4–7 days. The fermentation broth is extracted and purified to form a clear solution. The cosmetic is useful for whitening skin, or as a sunscreen. In an example G172 was grown at 25 deg for 5 days, centrifuged and maintained at −20 deg overnight to give a precipitate. The precipitate was filtered, and a skin lotion was prepared from the fermentation broth (10 wt. %), glycerol (5%), polyoxyethylene sorbitan monolaurate (1.5%), ethanol (10%), fragrance, antioxidant, antiseptic, pigment and purified water (6 pp)".

Japanese Patent No.JP07010736; 13.01.95; 128:66319 Coupland, Keith; Packer, Clarie Elizabeth (Croda International PLC; Coupland, Keith; Packer, Claire Elizabeth, UK) titled: "Sunscreen compositions comprising stearidonic acid and derivatives in combination with a UV blocking and/or absorbing material", describes "A sunscreen composition comprising a stearidonic acid, or a physiol. deriv. thereof, in combination with a UV blocking and/or UV absorbing material, is claimed. Also stearidonic acid may be used to treat inflammation caused by exposure to UV radiation, by exposure to sunlight or by burns. Thus, 10 kg of the seeds of *Echium plantagineum* were crushed and the oil was extracted with 15 L of petroleum ether. The petroleum ether extract was evaporated to yield 1741 g of golden yellow oil. The oil was converted to the corresponding fatty acid Me esters and used in sunscreens. A sunscreen oil was prepared containing Bu methoxydibenzoyl methane 2.0, octyl methoxy-cinnamate 7.5, benzophenone-3 4 5, PPG-2 myristyl ether propionate 10.0, above oil 2.0–10.0, perfumes, preservatives, and caprylic/capric triglycerides q.s. 100%.

Sophie Maisnier-patin and J. Richard, Station de Recherches Laitieres, Institut National de la Recherche Agronomique, Jouy-en-Joses, France, (Applied and Environmental Microbiology, May 1995, p. 1847–1852); titled: Activity and Purification of Linenscin OC2, an Antibacterial Substance Produced by *Brevibacterium linens* OC2, an Orange Cheese Coryneform Bacterium, describes: An orange cheese coryneform bacterium isolated from the surface of Gruyere of Comte and identified as *Brevibacterium linens* produces an antimicrobial substance designated linenscin OC2. This compound inhibits gram-positive food-borne pathogens including *Staphylococcus aureus* and *Listeria monocytogenes* but is not active against gram-negative bacteria".

Japanese Patent No.99-06310; titled: "A process for preparation of menaquinone-7 containing substance and food and drink preparations" describes: "A process is claimed for the preparation of menaquinone-7 (1) for use in food and drink preparations. (1) is produced by culturing *Bacillus subtilis* MR-141 (FERM P-14692), S-2 (IFO 14898, FERM BP-2528), ATCC 162 (FERM P-11052), F-2-01 (FERM P-9082) or their mutants in a liquid nutrient media at 30–40 deg, pH 6–8 for 2–4 days. The cells are removed by filtration and centrifuged. Both the cell pellet and the supernatant are dehydrated (e.g. by spray drying, lyophilization and drying in vacuo) in the absence of an organic solvent. The product is used for the prevention and treatment of osteoporosis (no clinical data disclosed) and is included in dried foods at 0.1–10% and drink preparations at 0.1–5%".

Most of the commercially available UV-blocking compounds in skin cream (sunscreen) are synthetic and the search for natural compounds with equal or greater efficiency is becoming more significant because of the consumer's preference for natural products.

The UV-absorbing properties of either the organisms or the extract have been extensively studied in higher plants, corals, cyanobacteria and other phytoplankton. Reference may be made to an UV absorbing (310 nm) compound that has been characterised from stem, bark and roots of mangrove plant, *Heritiera littoralis* (Bandaranayake WM 1994 phyto-chemical constituents and pigments in mangrove species and mangal associates of Northern Australia. Aust Inst Mar Sci Rep Townsville, Old Australia AIMS 19, 28 pp). The hyperoxic tissues of coral reefs also produce UV absorbing mycosporine like compounds (Dunlap WC Shick JM 1998. Ultraviolet radiation absorbing mycosporine-like amino acids in coral reef organisms: A biochemical and environmental perspective. J. Phycol. 34(3), 418–430). The induction and protective role of the UV-absorbing compounds such as mycosporine-like amino acids (MAAs) have been noted even in Florideophyceae (Franklin La., Yakovleva. I, Karsten U, Luenig, K 1999. Synthesis of mycoporine-like aminoacids in *Chondrus crispus*(Florideophyceae) and the consequences for sensitivity to ultraviolet B radiation. J. Phycol. 35, 682–693) Certain algae like *Dunaliella* are also known to possess intense carotenoid pigments to protect themselves against intense solar radiation. Some algae have other type of UV-absorbing (sunscreen) pigments like scytonemin (Proteau, P. J., Gerwick, W. H., Garcia-Pichel F. Castenholz 1993. The structure of scytonemin an ultraviolet sunscreen pigment from the sheath of cyanobacteria. Experientia 49, 825–829). These UV absorbing compounds are also known to be produced under photoinductive conditions and are dependant on temporal factors (Hannach G, Sigleo AC 1998. Photoinduction of UV absorbing compounds in six species of marine phytoplankton. Mar. Ecol. Prog Ser 174; 207–222). Though a number of papers have been published on the ultraviolet-absorbing/screening substances in cyanobacteria, phytoplankton and macroalgae and their role in mitigating ultraviolet toxicity (Sinha R P, Klisch M, Groeniger A, Haeder D P. 1998. Ultraviolet absorbing/screening substances in cyanobacteria, phytoplankton and macroalgae. J Photochem Photobiol B 47 J (2–3), 83–94) there have been only few publications on this aspect of bacteria (Arai T. Nishijima M, Adachi K Sano H 1992. Isolation and structure of a UV absorbing substance from the marine bacterium *Micrococcus* sp AK 334. Marine Biotech Inst Rep. Pp88–94 Japan). Sunscreen compositions comprising natural products of marine hydroid and derivatives thereof have been patented as useful sunscreening agents (lindquist, N.1. 1998 U.S. Pat. No. 5,705,146). A sunscreen/radioprotective compound has also been patented from fungus *Aspergillus versicolor* FK17 95-03294 (JP-06329576). Though bacteria possess a number of pigments that are supposedly photo protective only a few have been used for extracting UV A and B absorbing components. A fat-soluble UV absorbing compound F-1547 from *Paracoccus* sp has been patented (JP-11269175). A process for producing UV absorbing mycosporine-like aminoacids (MAA) from *Micrococcus* sp has also been developed (JP-06062878-A).

Antibacterial activity is widespread in microorganisms especially in those belonging to streptomycete group and many compounds from this group have been discovered and the processes and products have been patented. Ditrisaburicins A, B, and C from *Streptomyces cyaneus* are active against Gram-positive bacteria (Microb. Chem. Res. Found. EP-110155) For example CV 1 which is an antibacterial compound from *Streptomyces* sp is also used for sterilising instruments in hospitals (JP-J62000286). AAD-609 antibiotics produced by the fungus *Kibdelosporangium aridum* ATCC 3922 are inhibitory to Gram-positive bacteria (EP-218416). Narrow spectrum bactriocins from bacteria that are active against closely related species is common. Bacteriocins have wide-ranging applications in the food industry as preservatives (Eckner, K. F. 1992. Bacteriocins and Food Application. Dairy Food and Environ. Sanitation 12 (40), 204–209). Linenscin $OC_2$ is an antibacterial substance produced by the orange cheese coryneform bacterium *Brevibacterium linens* $OC_2$. It is bacteriolytic to *Listeria innocua*. (Boucabeille C. Menginlecreulx D. Henckes G. Simonet J M, Vanheijenoort J. 1997. Antibacterial and haemolytic activities of linocin $OC_2$ a hydrophobic substance produced by *Brevibacterium linens* $OC_2$. FEMS Microbiology Letters 153 (2), 295–301). The compound inhibits Gram-positive food-borne pathogen including *Staphylococcus aureus* and *Listeria monocyclogenes* but is not active against Gram-negative bacteria. A process for the production of antibacterial compound difficidin and its derivative is described where oxydifficidin is produced in large amounts compared with the other derivatives (U.S. Pat. No. 4,545,991; Zimmerman Sb, Schwartz C D, Monaghan R L, Pelak B A, Gillifillan E C 1987. Difficidin and Oxydifficidin; a novel broad-spectrum antibacterial antibiotics produced by *Bacillus subtilis* preparation and characterisation. J. Antibiot, 40 (12), 1677–1681.) These compounds have been shown to be active against *Klebsiella pneumonie*. Antibacterial compounds from bacteria, which are active against both Gram-positive and Gram-negative groups, are uncommon.

Some of the pigments in bacteria are also associated with antimicrobial activity. The use of antibiotic pigment violacein isolated from *Janthinobacterium lividum* (J P-10113169) or *Chromobacterium violaceum* and *Janthinobacterium* (JP-O6253864) has been patented. Pigments with antimicrobial properties have been isolated even from photosynthetic bacteria, *Chromatium purpuratum* (Burgess J G, Miyashita H, Sudo H, Matsunaga T 1991. Antibiotic production by marine photosynthetic bacterium *Chromatium purpuratum* NKPB 031704:localisation of the activity to the chromatophores FEMS Microbiol lett. 84 (3), 301–06). Cultures of aerobic marine bacterium *Alteromonas rubra* produce red pigments with pH indicator properties and a compound showing antibiotic activity against a variety of bacteria (Laatsch H and Thomson RH 1983. A revised structure for cycloprodigiosin. Tetrahedron Lett. 24 (26), 2701–04).

Though there have been reports on the occurrence of pigments alone or pigments with antibacterial activity in some of the microbes and sun screen compounds from yet others, there is no report available on the presence of all three in a single extract of a single bacterial species.

OBJECTS OF THE INVENTION

The main object of the present invention is to provide an alcoholic extract of novel bacterium isolated from deep-sea of coastal zone of Arabian Sea, Goa, India.

Another objects of the present investigation are to provide a process for the preparation of an alcoholic extract, having Carotenoids property, UV absorption, antibacterial and pH indicating properties.

Still another object of the invention is to use the extract from a deep-sea bacterium in food and cosmetics, which obviates the drawbacks as detailed above.

SUMMARY OF THE INVENTION

Accordingly the present invention provides a process for the preparation an alcoholic extract with Carotenoids, UV absorption, antibacterial and pH indicating properties from a deep-sea bacterium which comprises a method for growing the cells in a medium with salinity ranging from 1.5 to 3% for 3–4 days at 28+/−2° C. and harvesting them to prepare an extract which shows the properties of carotenoids (yellow/orange coloration), UV absorption, antibacterial and pH indicator properties.

DETAILED DESCRIPTION OF THE INVENTION

Accordingly, the present invention provides a novel deep-sea bacterium deposited with National Institute of Oceanography, Goa, India, having an accession no NIOCC isolate #222, and deposited on Aug. 19, 2003 with the Microbial Type Culture Collection and Gene Bank (MTCC), Institute of Microbial Technology, Sector 39-A, Chandigarh-160 036, India under the provisions of the Budapest Treaty for the International Recognition of the Deposit of Microorganisms for the Purpose of Patent Procedure having accession no MTCC 5114, which has similar properties to known *Brevibacterium casei* isolated from the deep sea at 5000 m depth waters of the Indian Ocean.

In one embodiment of the invention, the novel bacterium is a baroduric (pressure tolerant) one i.e. it is capable of growing both at 500 atm and at 1 atm pressure and the petroleum ether fraction of the bacterium when scanned in an UV visible spectrometer shows characteristic peaks at 448 nm with shoulders at 430 and 470 nm, which is similar to the carotenoid compound.

In another embodiment of the invention, the alcoholic extract of the said bacterium having caroteniods, UV absorption, anti bacterial, pH indicating properties.

In still another embodiment, the extract of the bacterium is used in many industrial applications, such as a food and beverages additive and food additive colour cum preservative.

The invention also describes a process for culturing the marine isolate for consistent cell biomass. Further, it elaborates the process of harvesting cells for bioactive pigments and associated radio protective constituents. This is the first time that a single extract of a baroduric marine isolate is being exploited for 3 different uses. The native extract of the culture is a pigment complex, which is yellow to orange in colour, has UV absorbing property and is antibacterial against some of the Gram-positive and Gram-negative bacteria.

The present investigation undertaken by the inventors has led to the preparation of single extract from a single bacterial isolate which shows multiple properties of colour, UV absorption, antibacterial property against both Gram-positive and Gram-negative bacteria, and pH indicator property. As a food additive, the preparation would not only add colour but also improve shelf life because of the antibacterial property. Further, it would also indicate deterioration by change in colour. This is the first time that a deep-sea isolate is used to prepare a single extract with multiple uses.

One more embodiment of the invention provides a process for the preparation of alcoholic extract of deep-sea bacterium isolated from the Indian coastal zones of Arabian sea, said process comprising isolating the bacterium and growing the cells in a medium with salinity ranging from 1.5 to 3% for 3–4 days at 28±2° C., centrifuging and washing with 1.5% NaCl, extracting with alcohol for 2–3 times and obtaining an extract which shows the properties of carotenoids (yellow/orange colour), UV absorption, antibacterial and pH indicator.

In another embodiment, the solvent used for extraction is an alcohol preferably methanol. In still another embodiment, the extract is used as UV (A, B, C) absorbing compound.

In still another embodiment, the extract inhibits growth of Gram-positive and Gram-negative bacteria.

In yet another embodiment, the yellow methanolic extract shows reversible colour change, being pink under alkaline and yellow under neutral or acidic conditions and is used as a pH indicator.

The present invention provides a process for the preparation an alcoholic extract with Carotenoids, UV absorption, antibacterial and pH indicating properties from a deep-sea bacterium for use in food and cosmetic industries which comprises a method for growing the cells in a medium with salinity ranging from 1.5 to 3% for 3–4 days 28+/−2° C. and harvesting them to prepare an extract which shows the properties of carotenoids (yellow/orange coloration), UV absorption, antibacterial and pH indicator properties.

In an embodiment of the present invention, the extract of bacterial cells obtained from the deep-sea is has carotenoid property.

In another embodiment of the present invention, the extract possesses UV absorbing property.

In yet another embodiment of the present invention, the extract has antibacterial agent characteristics.

In yet another embodiment of the invention, the extract inhibits growth of Gram-positive and Gram-negative bacteria.

In yet another embodiment of the invention, the yellow methanolic extract shows reversible colour change, being pink under alkaline and yellow under neutral or acidic conditions and is used as a pH indicator.

In another embodiment of the invention provides a composition for a sunscreen compound, said composition comprising, 25 to 75 mg methanolic extract of the bacterium claimed in claim 1, with 4 to 8 ml glycerol, 1 to 3 ml polyxylene sorbitan monolaurate, 5 to 15 ml ethanol and water q.s, preferably contains 50 mg methanolic extract of the bacterium, with 6 ml glycerol, 2 ml polyxylene sorbitan monolaurate, 10 ml ethanol and water q.s.

In yet another embodiment, the methanolic extract of novel bacterium is used for enhancing the color and shelf life of cheese or yoghurt.

In yet another embodiment, the amount of extract used for enhancing the color and shelf life of cheese and yoghurt ranging between 0.01 g/kg to 10 g/kg.

In yet another embodiment, the amount of extract used for enhancing the color and shelf life of cheese and yoghurt is 0.01 g/kg.

In another embodiment of the invention, dried methanolic extract is used for preparing menaquinone—7–8 containing substance, which are used in food and beverage and the quantity of extract used is in the range between 0.0001 to 0.001%.

Yet another embodiment provides a process for preparing menaquinone—7,8 containing substance, said process comprising growing the cells, for 2–5 days, harvesting after centrifugation and either spray drying or lyophilising and using at a concentration ranging between 0.5 to 10% for preventing and treatment of osteoporosis.

In yet another embodiment, the cells are grown for 4 days before harvesting.

BRIEF DESCRIPTION OF THE ACCOMPANYING DRAWINGS

In the drawings accompanying this specification.

The following examples are given by way of illustration and therefore should not be construed to limit the scope of the present invention.

EXAMPLE-1

Bacterial cells of the deep-sea isolate NIOCC isolate #222 were used to prepare methanol extract. The cells were crown in standard nutrient broth (Himedia Bombay) in 100% sea water (pH 7.5) for 3 days on a7 rotary shaker at 120 rpm at 28±2° C. The cells were collected by centrifugation at 5000 rpm and washed with 1.5% NaCl solution twice to remove the media. To the cells about 10 ml of 100% methanol was added and extracted overnight at 5° C. The supernatant is collected after centrifugation at 10,000×g for 10 minutes. The pellet was again extracted twice with 10 ml and twice with 5-ml quantities of methanol. The extracts were pooled and the volume was made up to 30-ml. This was concentrated in a flash evaporator at 40° C. to 8 ml. The example illustrates the method for the preparation of methanol extract from bacterial cells.

EXAMPLE 2

Figure 1:
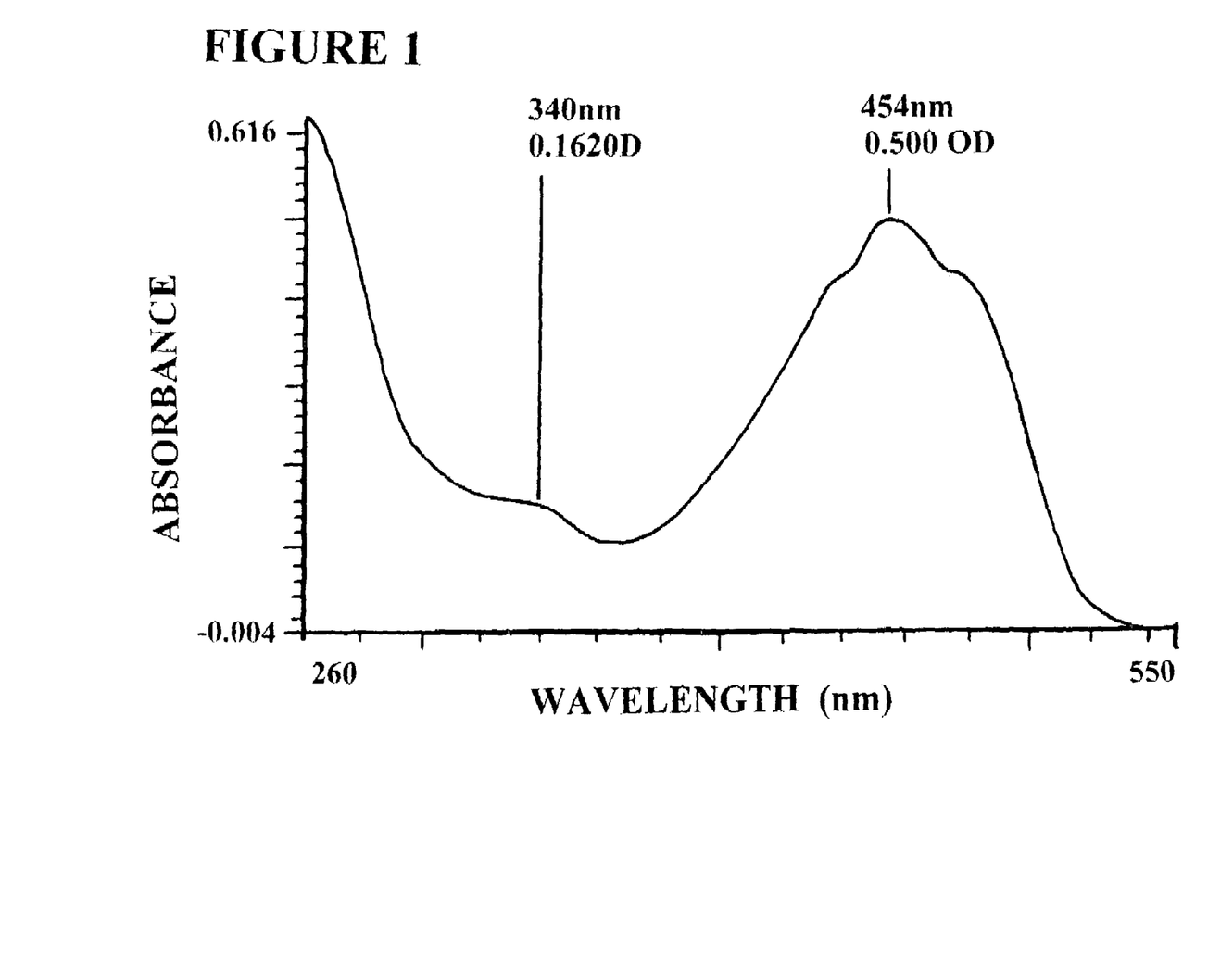
FIG. 1 represents the absorption spectrum of the extract.
Figure 2:
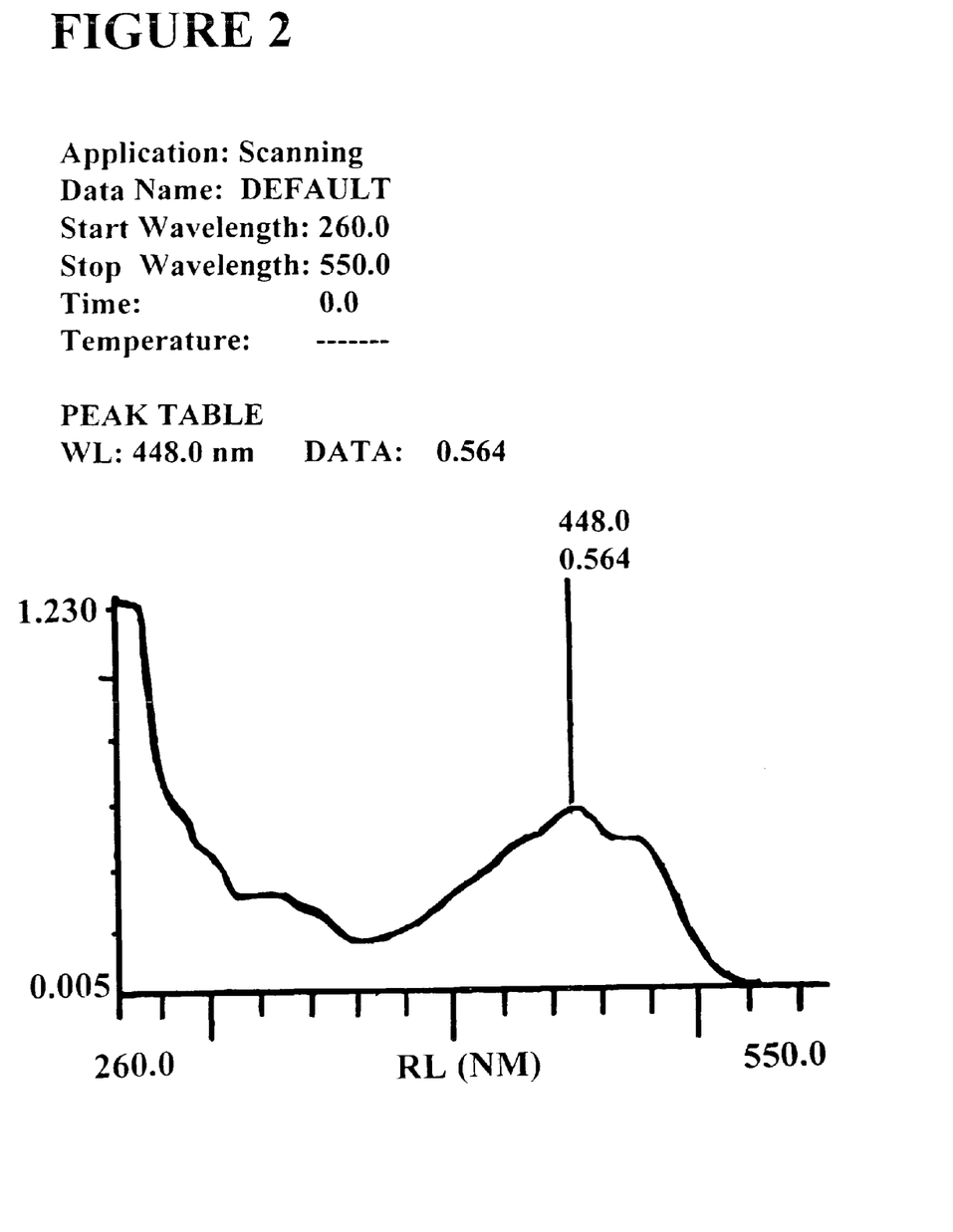
FIG. 2 represents the absorption spectrum of methanolic extract partitioned with petroleum ether.
Figure 3:
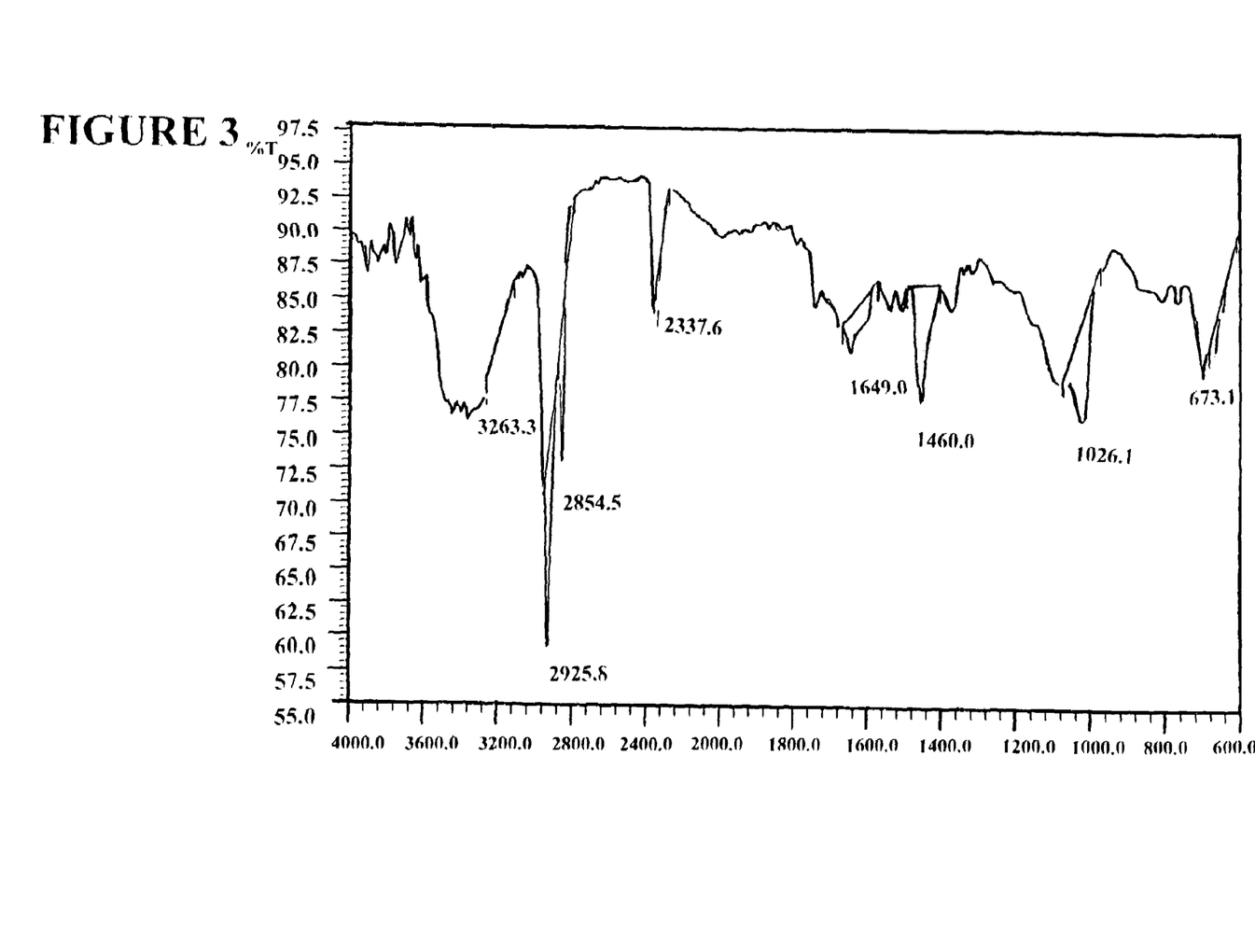
FIG. 3 represents the IR spectra of crude methanolic extract.
Figure 4A:
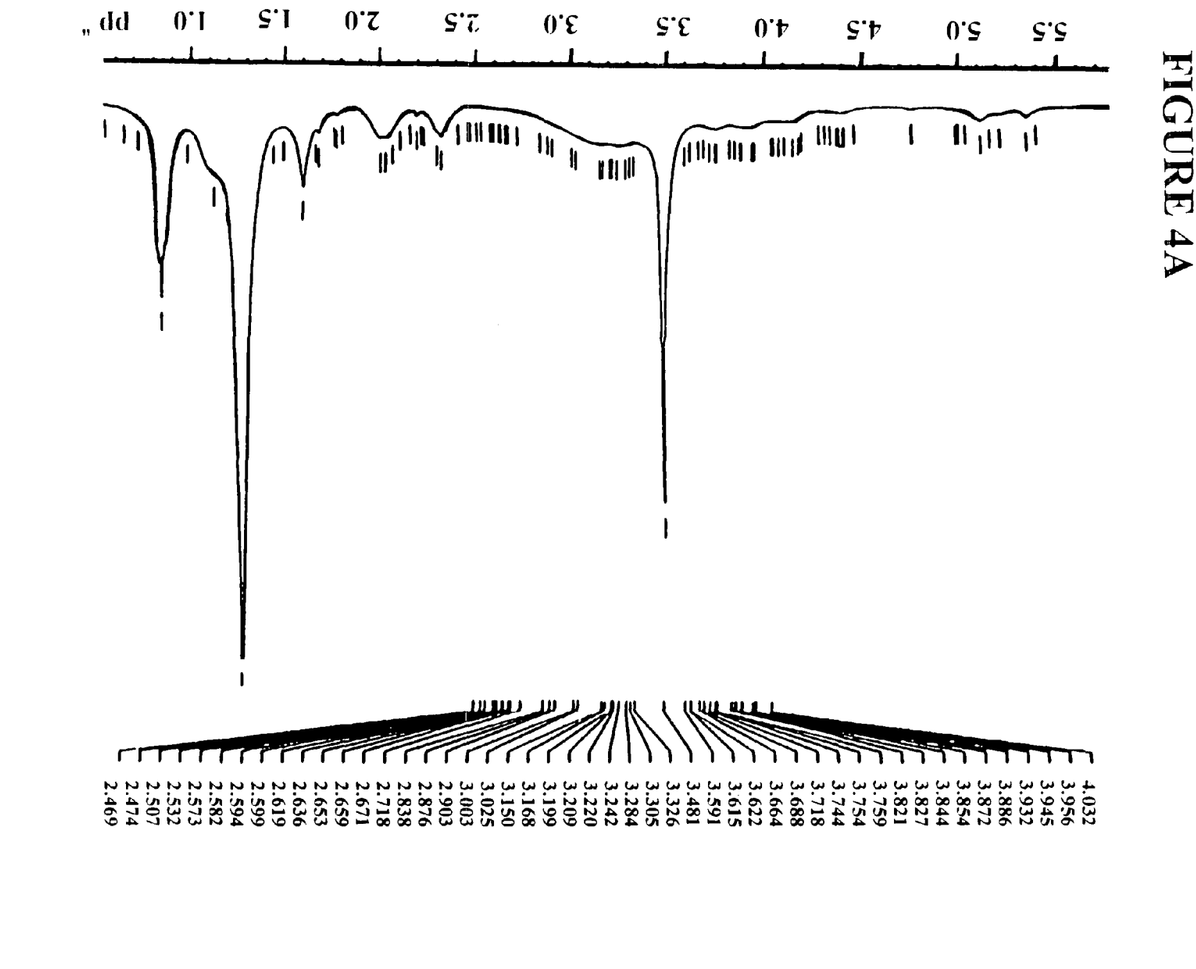
FIGS. 4A–4B represent the NMR spectra of crude methanolic extract.
Figure 4B:
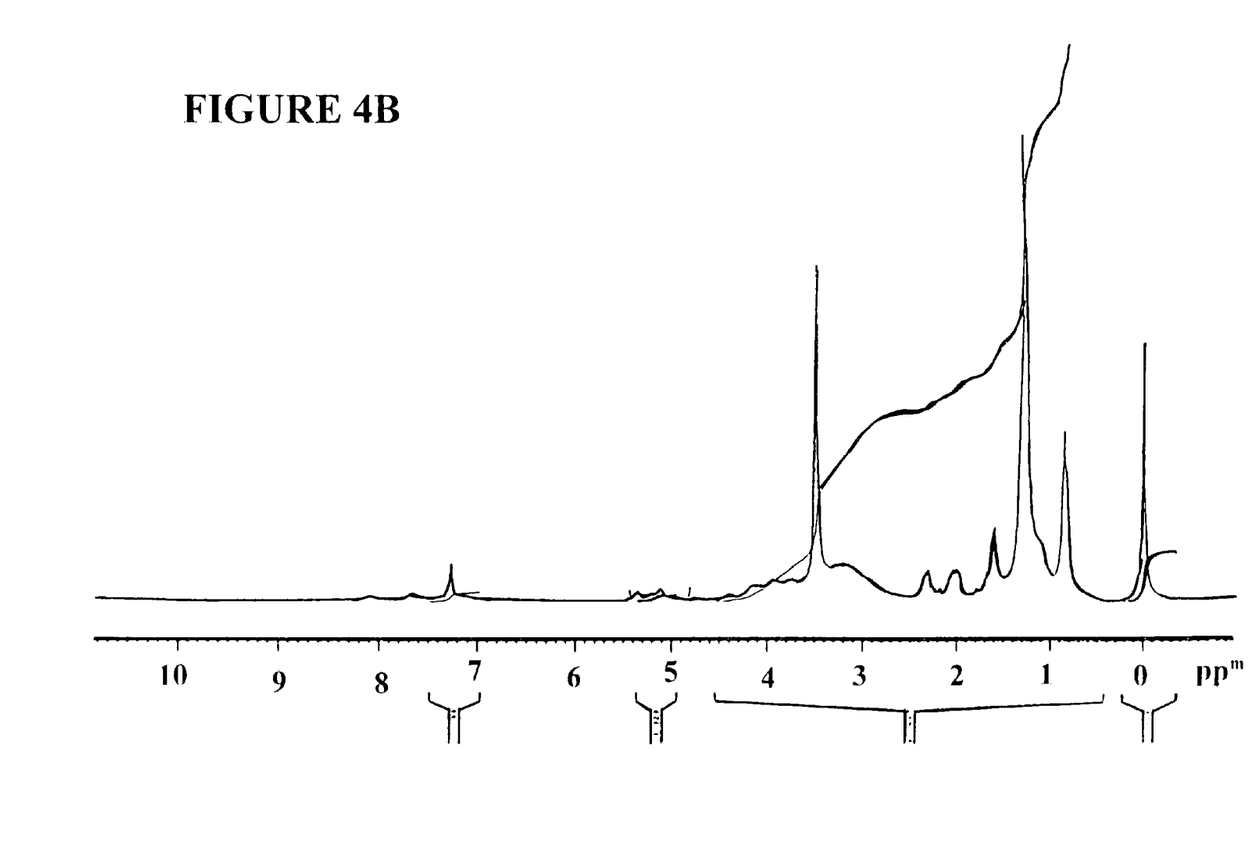

The methanol extract prepared as shown in Example 1 was scanned from 260 nm to 550 nm and it showed a peak at 454 nm with shoulders at 435 nm and 480 nm (FIG. 1). The same methanolic extract as shown in Example 1 was partitioned with 10-ml petroleum ether and scanned from 260 to 550 nm in a UV-visible spectrometer. In petroleum ether, peaks at 448 nm with shoulders at 430 and 470 nm showed that it is a caratenoid like compound (FIG. 2). IR and NMR spectra of crude methanolic extracts are given in FIGS. 3 and 4 4A–4B respectively.

EXAMPLE 3

A small quantity (100 μl) of the extractas shown in Example 1 was diluted to 4 ml with 100% methanol and scanned from 280 to 400 nm. UV absorbing property between 280 to 380 nm was observed with a peak at 340 nm (UVA). This property can also be seen in (FIG. 1). Absence of claims for such properties in other species of allied bacteria is shown in Table 3.

EXAMPLE-4

Washed suspensions of cells of *E. coli* and the candidate bacterial isolate used in the present invention were exposed to bright sunlight between 1100 to 1200 hrs and aliquots were plated at every 15 minute intervals. The current isolate could withstand the exposure and was cultivable even after 45' exposure to solar radiation having 5.75 mwcm$^{-2}$ at 312 nm (Table 1).

TABLE 1

| Survival of cultures when exposed to sunlight. | | |
|---|---|---|
| Time of exposure (minutes) | *E. coli* CFU.MI$^{-1}$ | Candidate culture CFU.MI$^{-1}$ |
| 0 (control) | 1.06 × 10$^8$ (±0.02)* | 4.72 × 10$^7$ (±0.75) |
| 15 | 1.72 × 10$^6$ (±0.56) | 5.41 × 10$^6$ (±0.36) |
| 30 | 3.36 × 10$^3$ (±0.32) | 2.34 × 10$^6$ (±0.80) |
| 45 | 0 | 7.68 × 10$^5$ (±1.28) |

CFU = Colony forming Units; Values in parenthesis show Std Deviation (SD)

EXAMPLE 5

The extract prepared as shown in Example 1 was tested for antibacterial properties against 2 Gram-positive (*Bacillus subtilus* and *Streptococcus aureus*) and 2 Gram-negative test cultures (*Escherichia. Coli* and *Pseudomonas aeruginosa*). Test cultures were grown overnightin 5 ml nutrient broth containing 0.8% agar to a density of 10$^{12}$ ml$^{-1}$ and poured over nutrient agar plates to form a lawn.

5 μl of methanolic extract prepared as shown in Example 1 was spotted over sterile antibiotic discs of 6 mm dia (Himedia, Mumbai) in triplicates. One of these discs was alkalinised by adding 2 μl of 0.1N NaOH and the other acidified by adding 2 μl of 0.1N HCl. On each lawn 3 discs in duplicate plates for each test culture were placed and incubated overnight at room temperature (28±2° C.). The zone of inhibition was measured. Controls for methanol, acid and base were also included. While *E. coli* was inhibited in the acidic and neutral pH, *Pseudomonas aeruginosa* was inhibited in all three pHs. *Bacillus subtilis* was inhibited in all three pHs but there was no effect on *Staphylococcus aureus* is shown in Table 2. Presence of such antagonistic properties in other species of bacteria is shown in table 3.

TABLE 2

Antibiotic activity (inhibition zone in mms) of the extract of the candidate bacteria.

| Volume of extract | Inhibition Zone | | | | | | | | | | | |
|---|---|---|---|---|---|---|---|---|---|---|---|---|
| | *E. coli* | | | *P. aerugenosa* | | | *S. aureus* | | | *B. subtlis* | | |
| | A | B | N | A | B | N | A | B | N | A | B | N |
| 5 μl | 6.2 | 0 | 6.2 | 6.4 | 6.7 | 6.4 | 0 | 0 | 0 | 6.4 | 6.7 | 6.4 |

A—Acidic
B—Basic &
N—Neutral

EXAMPLE-6

About 100 μl of 1 N NaOH was added to 1 ml of dilute methanol extract (1:4). Colour turned from yellow to pink. The colour was reversible with 1 N HCl. Thus it shows its pH indicator property.

EXAMPLE 7

A new cosmetic preparation contains methanolic extract of the bacteria 50 mg, Glycerol, 6.0 ml, polyoxyethylene sorbitan monolaurate 2.0 ml, ethanol, 10.0 ml, purified water q.s. to make 100 ml.

EXAMPLE 8

Dried methanolic extracts as described in example 1 are added at 0.01 g/kg of cheese or yoghurt to enhance colour and shelf life and found enhance the color as well as the shelf-life of the cheese.

EXAMPLE 9

The culture is grown for 4 days and the cells harvested after contrifugation. The cells are either spray dried or lyophilised and included at 0.5–0.1% concentration for prevention and treatment of osteoporosis. Dried methanolic extracts as described in example at 0.001% could also be used alternatively.

The Main Advantages of the Present Invention Are:

1. The preparation could be used as a food additive that
  a) augments colour;
  b) improves shelf life by inhibiting both Gram-positive and Gram-negative bacteria; and
  c) indicates spoilage by colour change.

2. The preparation could be used in skin cream/lotion not only as a radio protectant but also for preventing acne.

3. As only one culture is used for all the properties, the necessity to cultivate multiple organisms is eliminated. This is definitely a great advantage for commercial preparation.

TABLE 3

| Sl. No | Property | *Brevibacterium* spp 2, 4, 5, 6 | *B linens* 1 | *B iodinum* 2 | *B. epidermis*/ *B. casei* 2 | *B. acetylicum* 2 | *B. halotoleran* 2 | *B maris* 3 | *B.* (NIO) |
|---|---|---|---|---|---|---|---|---|---|
| 1 | Colour | +/− | + | + | − | − | − | − | + |
| 2 | antibacterial | +/− | + G +ve | + | + | +/− | − | + | + G +ve and G −ve |
| 3 | UV absorbing compound | − | − | − | − | − | − | − | + |
| 4 | UV + Color | − | − | − | − | − | − | − | + |
| 5 | UV + antimicrobial | − | − | − | − | − | − | − | + |
| 6 | UV + Antimicrobial + Color | − | − | − | − | − | − | − | + |

Ref:
1. Doucaheille C, Menginlecreulx D, Henckes a, Simonet JM and Vaneijenoort J 1997. Antibacterial and hemolytic activities of linenscin OC2 a hydrophobic substance produced by *Brevibacterium linens* OC2. FEMS Microbiology Letters 153 (2): 295–301.
2. Jones D and Keddie R. M. (1985). Genus *Brevibacterium* p 1301–1313. Sheath PHA, Mair, NA Shape, ME and Glott J.G. (ed). In Bergey;s manual of systemic bateriology, Vol. 2 Williams and Wilkins, Baltimore.
3. Kato F, Yoshimi M, Araki, k Motomura y Matsufune Y, Nobunaga H 1984. 'Screening of bacteriocins in amino acid or nucleic acid producing bacteria and related species.
4. Nelis HJ De Leenheer AP (1991). Microbial sources of carotenoid pigments used in foods and feeds. J Appl Bacteriol 70, 3, 181–91.
5. Nelis HJ De Leenheer AP (1989). Reinvestigation hi *Brevbacterium* sp. strain KY 4313 as a source of canthaxanthin. Appll Environ. Microbiol 55, 10, 2505–10.
6. Villadsen IS 1992. Microorganisms producing high levels of carotenoid, especially astaxanthin. Wo-9222648.23.12.92. PR 14.06.91-DK 001151; 15.06.92 as DK 0186.

The invention claimed is:

1. An isolated deep-sea bacterium deposited with the National Institute of Oceanography, Goa, India, having accession no. NIOCC isolate #222, and deposited with the Microbial Collection and Gene Bank (MTCC) having accession no. MTCC 5114, which isolated deep-sea bacterium was isolated from the deep sea at 5000 m depth waters of the Indian Ocean.

2. The isolated deep-sea bacterium as claimed in claim 1 wherein the isolated deep-sea bacterium is baroduric.

3. The isolated deep-sea bacterium as claimed in claim 1 wherein a petroleum ether fraction of the isolated deep-sea bacterium scanned in an UV visible spectrometer shows characteristic peaks at 448 nm with shoulders at 430 nm and 470 nm, which are similar to characteristic peaks of a carotenoid compound.

4. The isolated deep-sea bacterium as claimed in claim 1 wherein an alcoholic extract of the isolated deep-sea bacterium has carotenoid, UV absorption, anti bacterial, and pH indicating properties.

5. The isolated deep-sea bacterium as claimed in claim 4 wherein the extract of the isolated deep-sea bacterium is used as a food and beverages additive and preservative.

* * * * *